United States Patent [19]
Congleton et al.

[11] Patent Number: 5,817,271
[45] Date of Patent: Oct. 6, 1998

[54] ALTERING THE SURFACES OF FUNCTIONAL ABSORBENT MATERIALS FOR USE IN ABSORBENT ARTICLES

[76] Inventors: Stephen D. Congleton; Yousef G. Aouad; Jerry L. Dragoo; Bradley E. Walsh, all of The Procter & Gamble Company, Winton Hill Technical Center 6100 Center Hill Ave., Cincinnati, Ohio 45224

[21] Appl. No.: 769,460

[22] Filed: Dec. 18, 1996

[51] Int. Cl.[6] ............................ B29C 59/02; B29C 59/16; B23K 26/00

[52] U.S. Cl. .................... 264/400; 219/121.68; 264/482; 264/138; 264/293; 425/174.4

[58] Field of Search ..................................... 264/400, 482, 264/1.37, 138, 293; 219/121.68, 121.69, 121.66; 425/174.4

[56] References Cited

U.S. PATENT DOCUMENTS

| | | |
|---|---|---|
| 3,790,744 | 2/1974 | Bowen ..................................... 264/482 |
| 3,881,490 | 5/1975 | Whitehead et al. . | |
| 4,307,046 | 12/1981 | Neefe ..................................... 264/1.37 |
| 4,795,452 | 1/1989 | Blaney et al. . | |
| 4,840,692 | 6/1989 | Kamstrup-Larsen . | |
| 5,300,053 | 4/1994 | Genaro . | |
| 5,441,836 | 8/1995 | Balz et al. ............................... 264/1.37 |
| 5,536,264 | 7/1996 | Hsueh et al. . | |

*Primary Examiner*—Mathieu D. Vargot
*Attorney, Agent, or Firm*—Theodore P. Cummings; Steven W. Miller; Jacobus C. Rasser

[57] ABSTRACT

The method relates to functional absorbent materials that are profiled through cutting and heating to form flow channels, and in one embodiment to form bellows which rise above the flow channels. Additionally, the flow channels which are partially cut into an absorbent material may also function as hinge means for that material as regards bending and conformity of fit. In one embodiment, functional absorbent material is provided with discrete heating and cutting, e.g., by a laser, by which channels and bellows are simultaneously formed. In another embodiment using a discrete heating and cutting means, e.g., a laser, is used to provide channels partially through the surface of a functional absorbent material.

19 Claims, 4 Drawing Sheets

ALTERING THE SURFACES OF FUNCTIONAL ABSORBENT MATERIALS FOR USE IN ABSORBENT ARTICLES

FIELD OF THE INVENTION

The present invention relates to functional absorbent materials that are profiled through cutting and heating to form flow channels, and in one embodiment to form bellows or raised portions which rise above the flow channels. Additionally, the flow channels which are partially cut into a functional absorbent material may also function as hinge means for that material as regards bending and body conformity.

BACKGROUND OF THE INVENTION

Absorbent pads fabricated of air-laid fibers and disposable diapers, incontinent briefs, sanitary napkins using such pads are well known in the prior art. In addition, such pads having directional flow means for fluid or channels for fluid flow are also well known. U.S. Pat. No. 3,575,174, entitled "Sanitary Napkin", issued Apr. 20, 1971 to Mogor describes an absorbent core made from conventional materials such as absorbent cotton, wood pulp fibers, paper wadding, cellulosic fibers and/or synthetic fibers that has been embossed from the top surface (i.e., top sheet) to provide channels. Besides embossment, channels have been formed into such conventional absorbent cores through the top surface of the absorbent article. U.S. Pat. No. 3,871,378, entitled "Absorbent Bandage", issued on Mar. 18, 1975 to Duncan et al. describes a pad having a central portion which has been depressed by a steel rod. Additional means of creating such channels for fluid flow are described in U.S. Pat. No. 3,881,490, entitled "Thin, Flexible Absorbent Pads", issued on May 6, 1975 to Whitehead et al. which describes the creation of channels by heat and pressure. Further means for creating such channels are described in U.S. Pat. No. 4,079,739 entitled "Die-Cut Contoured Catamenial Napkin Of Multi-Layered Construction", issued on Mar. 21, 1978 to Whitehead which discloses cutting an absorbent pad to form flow channels.

Therefore, embossing, impressing, providing heat and/or pressure and cutting are known means to provide channels in conventional absorbent pad structures. However, what has been previously unknown has been the providing of such flow channels to functional absorbent materials as described herein. Additionally, what has not been known is the effect, i.e., the benefit, produced by using a discrete heating/cutting means, such as a laser, on a functional absorbent material.

Functional absorbent materials are disclosed in U.S. Pat. No. 5,387,207, issued to Dyer, et al.; U.S. patent application Ser. No. 08/370,922 (DesMarais, et al.) entitled "Absorbent Foam Materials For Aqueous Fluids Made From High Internal Phase Emulsions Having Very High Water To Oil Ratios", abandoned; U.S. patent application Ser. No. 08/484,727 (DesMarais, et al.) entitled "Foam Materials For Insulation Derived From High Internal Phase Emulsions", now U.S. Pat. No. 5,770,634; and U.S. Pat. No. 5,563,179, issued to DesMarais, et al. which are hereby incorporated herein by reference.

Thus it is an object herein to produce channels in functional absorbent materials through any one of the means disclosed herein.

It is a further object to produce channels and bellows which border such channels in functional absorbent materials.

It is also an object to provide channels in absorbent core structures comprising conventional materials through cutting by a laser.

SUMMARY OF THE INVENTION

Accordingly, the present invention relates to a method of providing finite expansion to regions of a functional absorbent material that herein is preferably used in a disposable absorbent article. The method comprises the steps of subjecting a functional absorbent material to a heat source that provides localized heating such that only finite expansion of the functional absorbent material occurs about areas of heating. In one embodiment the functional absorbent material is heated along one or more discrete regions or lines of heating. More specifically, a functional absorbent material is delivered to a localized heat source, preferably being a laser. The heat source is focused along at least one line of heating of the functional absorbent material. It should be noted that each line of heating initially resides on the surface of the functional absorbent material but can go through the surface down into the interior portions of the functional absorbent material and can be in any direction, orientation or shape conceivable. Next, the heat source is activated along one or more lines of heating. For each line of heating, the top surface of the functional absorbent material is vaporized, thereby causing the functional absorbent material to be cut at least partially through to create a flow channel. Simultaneous to the vaporization, the functional absorbent material is heated in the region immediately adjacent to the line of heating, and the functional absorbent material expands outwardly from the channel due to the heating of these adjacent regions, thereby forming bellows or raised portions on either side of each channel.

From the vaporization of the functional absorbent material along the line of heating and the expansion of the adjacent or surrounding regions of the functional absorbent material, flow channels are formed. The flow channels are the primary venues of fluid transport from one location of the functional absorbent material to another location of the functional absorbent material. Additionally, when a functional absorbent material herein is heated with a localized heat source, finite areas on either side of the flow channels expand above the originally flat surface of the functional absorbent material. These expanded regions function as partial borders or barriers and guides to fluid transport along the flow channels. Preferably, two expanded regions will form on either side of a flow channel (i.e., line of heating) and thus will be substantially parallel to and juxtaposed to the flow channel.

In another embodiment of a functional absorbent material, one or more lines of heating are formed by a localized heat source for the purpose of forming hinge means within the functional absorbent material. At such forming, the hinge means operate to allow folding along the hinge means in the functional absorbent material. When the functional absorbent material is part of a non-rigid structure like a disposable absorbent article, improved fit and containment of the article can be achieved in part due to folding of the functional absorbent material about its hinge means.

Also provided herein is a method for increasing the effective surface area of a functional absorbent material. The method comprises the steps of providing a functional absorbent material to a scoring means, preferably being a laser. The functional absorbent material is then scored in prescribed locations thereby producing depressed regions within the surface of the functional absorbent material to facilitate fluid flow and increase the effective surface area of the functional absorbent material. A preferable scoring means is a laser providing sufficient intensity and power to cut away portions of the functional absorbent material.

Another embodiment herein provides a method of profiling a functional absorbent material within an absorbent article. The method comprises the steps of delivering an absorbent article comprising a topsheet, a backsheet joined to the topsheet, and a functional absorbent material that is positioned between the topsheet and the backsheet to a localized heating source. Heat is applied to the localized heating source through the topsheet or backsheet to the functional absorbent material such that the localized heating source provides localized heating to the functional absorbent material to finitely expand and/or score the functional absorbent material.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 1:
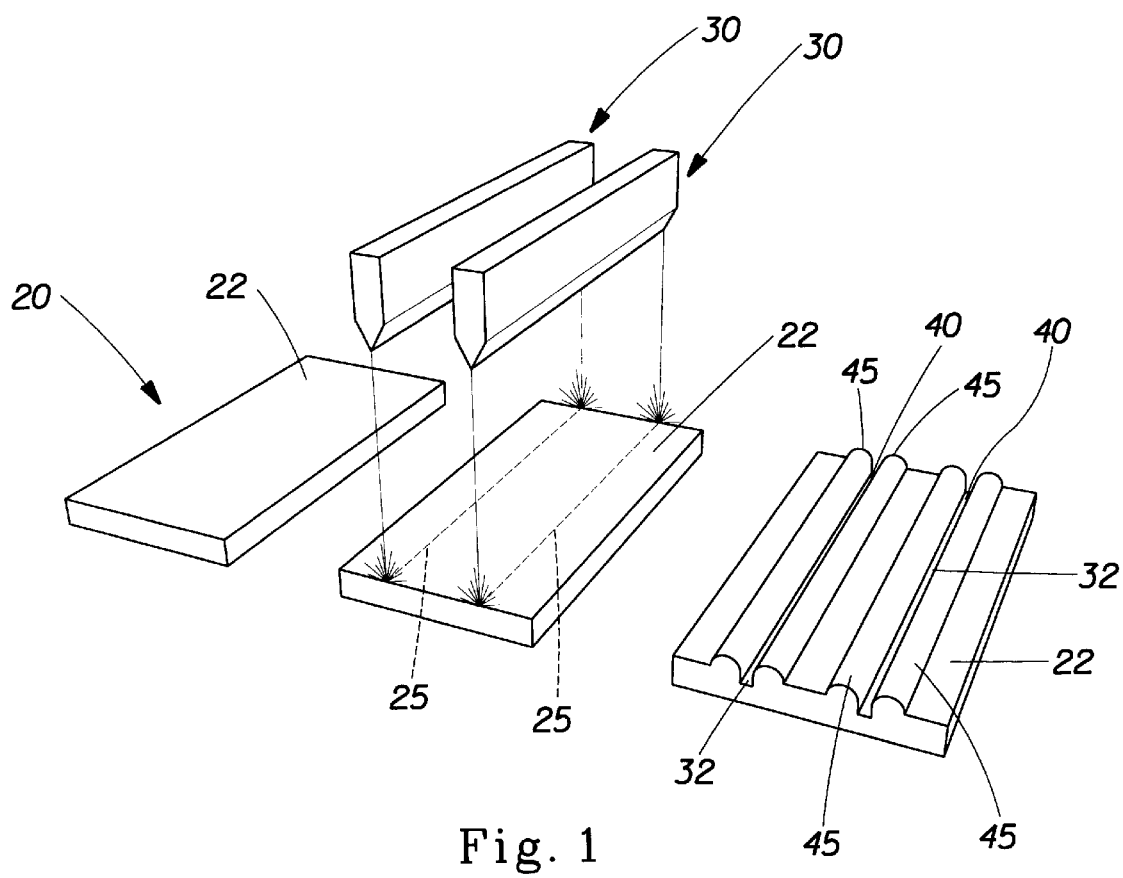
FIG. 1 provides a perspective view of a functional absorbent material in three stages from delivery, heating, and to creating channels and bellows.

The present invention provides a method of providing finite expansion to regions of a functional absorbent material or absorbent foams that are preferably used in a disposable absorbent article. The steps of the method comprise subjecting a functional absorbent material to a heat source that provides localized heating such that only finite expansion of the functional absorbent material occurs about the areas of heating. More specifically, the functional absorbent materials herein are altered from their surfaces by a localized heating source. By the term "functional absorbent material" or "absorbent foam" it is meant herein those foam materials formed from High Internal Phase Emulsions (hereinafter referred to as "HIPEs"). Preferably, the HIPE foams have a volume to weight ratio of water phase to oil phase in the range of from about 55:1 to about 100:1 as described in U.S. Pat. No. 5,650,222 (Thomas A. DesMarais, et al.), filed Nov. 29, 1995 and is incorporated by reference herein. Alternatively, the HIPE foams have a volume to weight ratio of water phase to oil phase in ranges less than 55:1. Such foams are described extensively in the literature, for example in U.S. Pat. No. 5,387,207 issued to Dyer et al. on Feb. 7, 1995 and is hereby incorporated herein by reference. As shown in FIG. 1, the functional absorbent material 20 is heated along one or more discrete regions or lines of heating 25. More specifically, a functional absorbent material 20 is delivered to a localized heat source 30, preferably being a laser 36 (not shown). The heat source 30 is focused along at least one line of heating 25 of the functional absorbent material. It should be noted that each line of heating 25 resides on the surface 22 of the functional absorbent material 20 and can be in any direction, orientation or shape conceivable. Next, the heat source 30 is activated along one or more lines of heating 25. For each line of heating 25, the surface 22 of the functional absorbent material 20 is vaporized, thereby causing the functional absorbent material 20 to be cut at least partially through to create a flow channel 40. Simultaneous to the vaporization of the surface 22 along the line of heating 25, the functional absorbent material 20 is heated in the region immediately adjacent to the line of heating 25, and the functional absorbent material 20 expands outwardly from the channel 40 due to the heating thereby forming raised portions or bellows 45 on either side of channel 40. While not wishing to be bound by any particular theory, it is believed that these raised portions 45 are formed due to the heat energy transferred from the line of heating 25 that releases moisture in immediate surrounding regions on either side of the line of heating 25 to produce an expansive effect in these regions of the functional absorbent material 20. It should be noted that this expansive effect should occur for all HIPE foam ratio types discussed previously where the heat source 30, preferably being a laser 36, provides the right power, focus and/or intensity to any functional absorbent material herein.

Figure 1A:
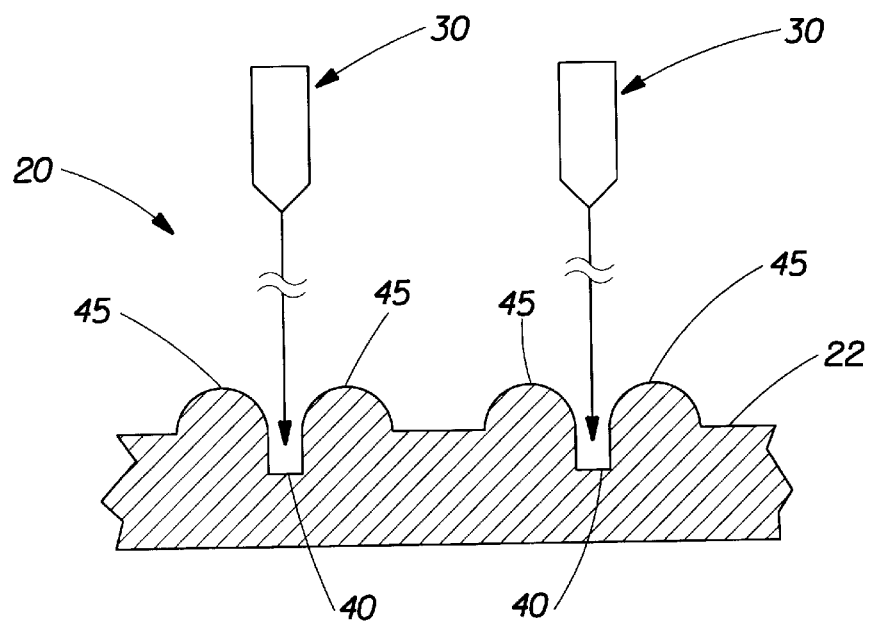
FIG. 1A shows a cross-sectional view of the creation of channels and bellows in FIG. 1.

From the vaporization of the functional absorbent material 20 along a line of heating 25 and the expansion of the surrounding regions of the functional absorbent material 20, flow channels 40 and bellows 45 are formed. The flow channels 40 are the primary venues of fluid transport from one location of the functional absorbent material 20 to another location of the functional absorbent material 20. Additionally, when a functional absorbent material 20 herein is heated with a localized heat source 30, finite areas on either side of the flow channels 40 expand above the surface of the functional absorbent material thereby forming the raised bellows 45 as seen in FIGS. 1 and 1A. These bellows 45 function as partial borders or barriers and guides to fluid transport along the flow channels 40. Preferably, a pair of bellows 45 will form on either side of a flow channel 40 (i.e., from a line of heating 25) and thus will be substantially parallel and juxtaposed to the flow channel.

FIG. 1 shows the functional absorbent material 20 being heated in the cross-direction, i.e., perpendicular to the machine direction. It should be noted that such heating would most preferably be done in the machine direction. FIG. 1 is presented thus to provide visual understanding of the heating of the functional absorbent material 20 and the forming of channels 40 and bellows 45.

FIG. 1A shows the functional absorbent material 20 of FIG. 1 in cross-section. In this view, it can be clearly seen that as the localized heat source 30 vaporizes the surface 22 of a functional absorbent material 20 along a line of heating 25, a channel 40 will be formed. Also, it should be noted that this channel 40 will preferably be positioned at a distance below the top surface 22 of the functional absorbent material 20. Alternatively, the channel 40 can be at a similar surface level to the other un-heated surfaces 22 of the functional absorbent material 20.

In another embodiment of a functional absorbent material 20, one or more lines of heating 25 are formed by a localized heat source 30 for the purpose of forming hinge means 32 (FIG. 1) within the functional absorbent material 20. At such forming, the hinge means 32 can operate to allow folding along these means 32 in the functional absorbent material 20. When the functional absorbent material 20 is part of a non-rigid structure like a disposable absorbent article, improved fit and containment of the article can be achieved in part due to folding of the functional absorbent material 20 about its hinge means 32. It should be noted herein that the hinge means 32 are the same in scope and characteristic as the channels 40 formed herein. In this embodiment, at least one of the channels is specifically and/or additionally used as a hinge means 32 and does not function only as a flow channel 40.

The method for increasing the surface area of a functional absorbent material 50 herein comprises providing that functional absorbent material 50 to a scoring means 60, preferably being a laser whose power, intensity and/or focus are not such that the functional absorbent material 50 will expand upon contact. Note, the object for this embodiment is to score the surface of the functional absorbent material 50 and not cause expansion on its surface. However, it should be again noted that functional absorbent materials 50 may expand as the functional absorbent materials 20 given the required power, intensity and/or focus of a heat source, preferably being a laser. The functional absorbent material 50 is then scored in prescribed locations thereby producing depressed regions or channels 70 within the surface of the functional absorbent material 50 to facilitate fluid flow and increase the effective surface area of the functional absorbent material 50. A preferable scoring means 60 is a laser that provides sufficient intensity, focus and power to cut away portions of the functional absorbent material 50.

Figure 2:
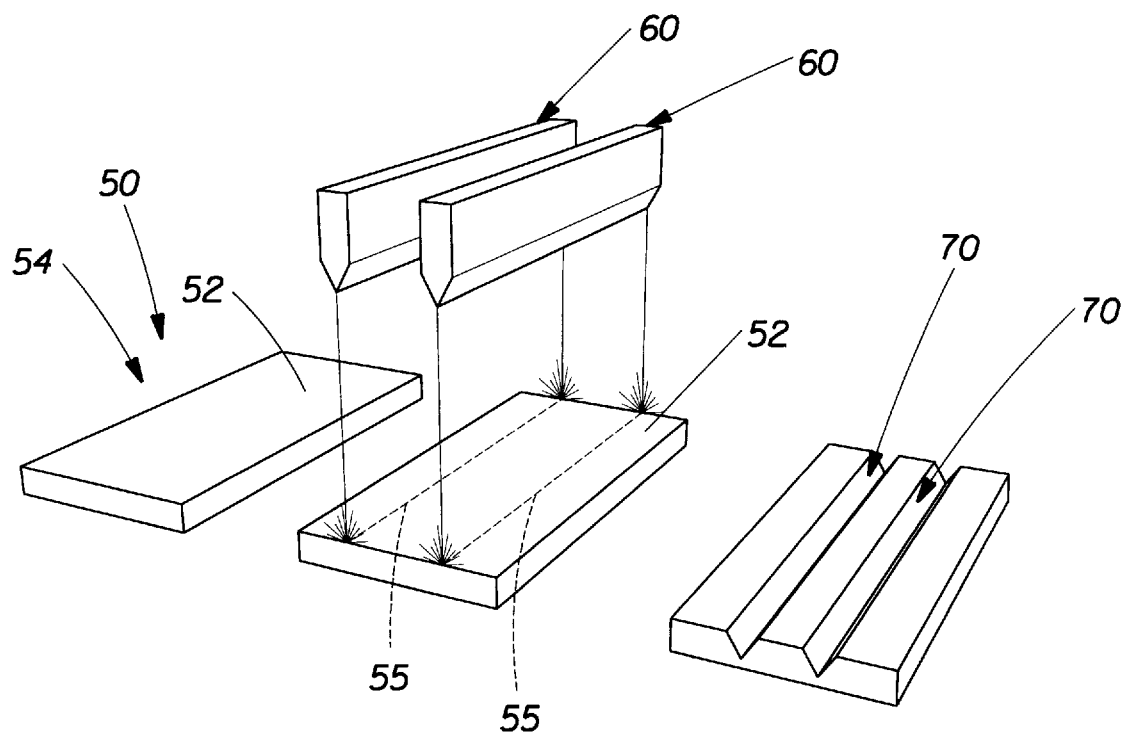
FIG. 2 provides a perspective view of a functional absorbent material in three stages from delivery, heating, and to creating channels.

FIG. 2 shows the functional absorbent material 50 being scored in the cross-direction, i.e., perpendicularly to the machine direction. It should be noted that such scoring would most preferably be done in the machine direction. FIG. 2 is presented thus to provide visual understanding of the scoring of the functional absorbent material 50 and the forming of channels 70.

As discussed above, the preferable scoring means is a laser and most preferably a $CO_2$ laser. When a $CO_2$ laser beam is focused on a functional absorbent material 50, the laser will preferably cut the functional absorbent material 50 to a certain depth. The cut depth is related to web speed, laser power (including intensity and wattage) and laser focus, all of which are determined by a manufacturer. By orienting the cuts in a particular pattern the acquisition properties of the absorbent core can be improved. The cuts increase the available surface area of the functional absorbent material 50 by creating channels 70 within the functional absorbent material 50 which provide at least two additional surfaces within the functional absorbent material 50 for acquisition of exudates. Therefore, scoring such a functional absorbent material 50 can increase exudate acquisition. By the term "exudates" it is meant herein those fluid, solid, and semi-solid wastes resulting from the anal and/or vaginal cavities of wearers. The channels 70 in the functional absorbent material 50 can also impede the motion of fluid-like material, such as runny BM which requires great acquisition time over fluids.

Figure 2A:
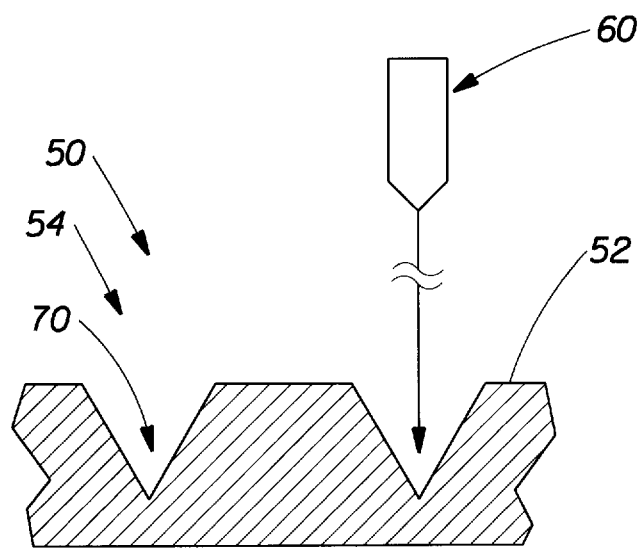
FIG. 2A provides a cross-sectional view of the creation of channels in FIG. 2.
Figure 3A:
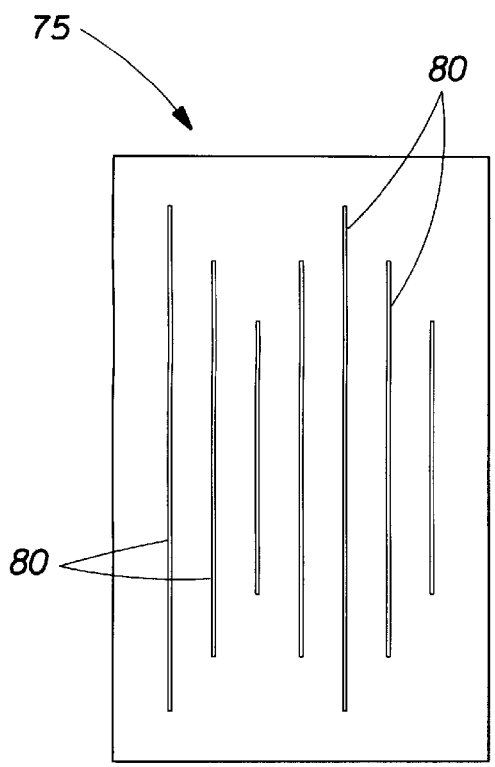
FIG. 3A shows a channel pattern herein.
Figure 3B:
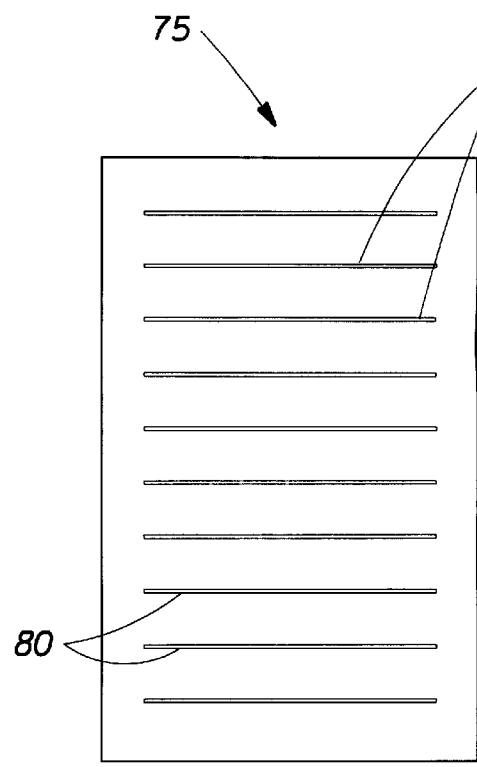
FIG. 3B shows a channel pattern herein.
Figure 3C:
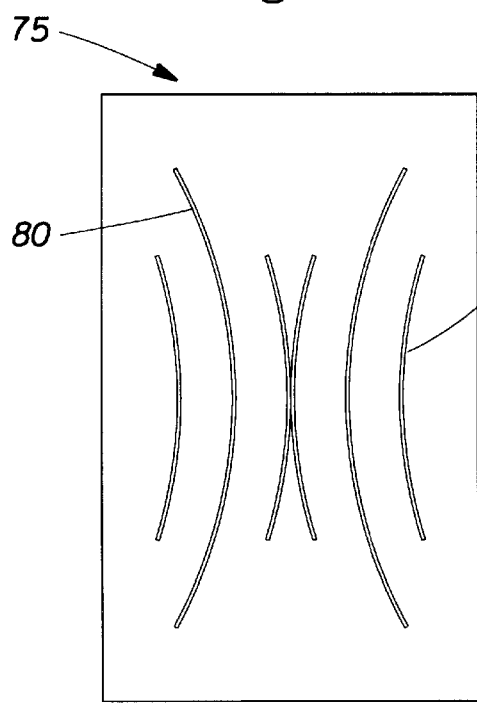
FIG. 3C shows a channel pattern herein.
Figure 3D:
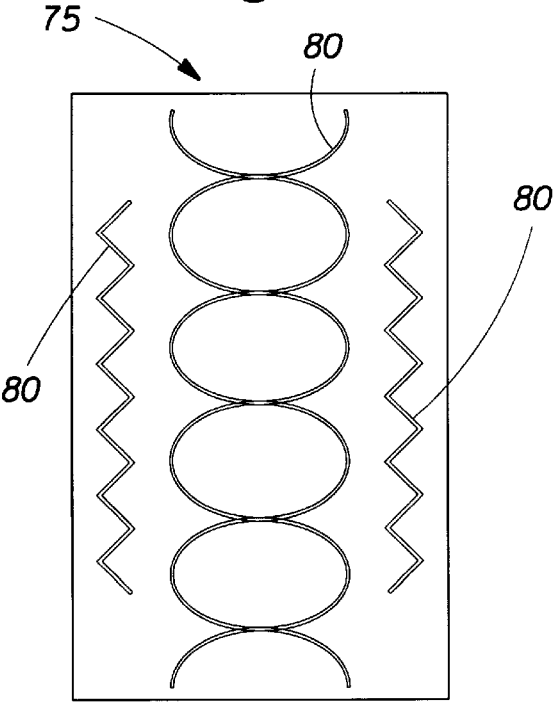
FIG. 3D shows a channel pattern herein.

FIG. 2A discloses the scored functional absorbent material 50 in cross-section. As can be clearly seen from this perspective, the scoring means 60, preferably being a laser, scores or cuts through the surface layer 52 of the functional absorbent material 50 to create a channel 70. The channels 70 can be used to transport fluid from one portion of the functional absorbent material 50 to another. Also, the channels 70 provide additional surface area to a previously planar surface. This additional surface area increases fluid acquisition across the functional absorbent material 50 and also distribution through the functional absorbent material 50. In one embodiment, the scored functional absorbent material 50 can be positioned between a topsheet and an acquisition layer or absorbent core such that fluid contacting the topsheet will be drawn toward and quickly dispersed by the scored functional absorbent material 50; i.e., the fluid is quickly dispersed down through the scored functional absorbent material 50 to the underlying acquisition layer and/or absorbent core.

FIGS. 3A, 3B, 3C and 3D disclose embodiments configurations and orientations of channels 80 which may used in a functional absorbent material 20 or functional absorbent material 50. As can be seen from the foregoing, the channels 80 in absorbent material 75 may be linear, curvilinear and/or a combination of the two. Also, channels 80 may be aligned vertically, horizontally or at any angle or direction therebetween. Selection of the appropriate channel 80 design is within the purview of a manufacturer according to specifications in his/her absorbent articles.

Polymeric foams according to the present invention useful in absorbent articles and structures are those which are relatively open-celled. This means the individual cells of the foam are in complete, unobstructed communication with adjoining cells. The cells in such substantially open-celled foam structures have intercellular openings or "windows" that are large enough to permit ready fluid transfer from one cell to the other within the foam structure. Such open-celled foams are disclosed in U.S. Pat. No. 5,550,167, "Absorbent Foams Made High Internal Phase Emulsions Useful For Acquiring Aqueous Fluids" issued to DesMarais on Aug. 27, 1996; U.S. Pat. No. 5,387,207, "Thin-Unit-Wet Absorbent Foam Materials For Aqueous Body Fluids And Process For Making Same" issued to Dyer et al. on Feb. 7, 1995; and U.S. Pat. No. 5,260,345, "Absorbent Foam Materials For Aqueous Body Fluids And Absorbent Articles Containing Such Materials" issued to DesMarais et al. on Nov. 9, 1993 each of which is incorporated herein by reference.

These substantially open-celled foam structures will generally have a reticulated character with the individual cells being defined by a plurality of mutually connected, three dimensionally branched webs. The strands of polymeric material making up these branched webs can be referred to as "struts". For purposes of the present invention, a foam material is "open-celled" if at least 80% of the cells in the foam structure that are at least 1 $\mu$m in size are in fluid communication with at least one adjacent cell.

In addition to being open-celled, these polymeric foams are sufficiently hydrophilic to permit the foam to absorb aqueous fluids in the amounts specified hereafter. The internal surfaces of the foam structures are rendered hydrophilic by residual hydrophilizing surfactants left in the foam structure after polymerization, or by selected post-polymerization foam treatment procedures, as described hereafter.

The extent to which these polymeric foams are "hydrophilic" can be quantified by the "adhesion tension" value exhibited when in contact with an absorbable test liquid. The adhesion tension exhibited by these foams can be determined experimentally using a procedure where weight uptake of a test liquid, e.g., synthetic urine, is measured for a sample of known dimensions and capillary suction specific surface area. Such a procedure is described in greater detail in the TEST METHODS section of U.S. Pat. No. 5,387,207 (Dyer et al), issued Feb. 7, 1995, which is incorporated herein by reference. Foams which are useful as absorbents in the present invention are generally those which exhibit an adhesion tension value of from about 15 to about 65 dynes/cm, more preferably from about 20 to about 65 dynes/cm, as determined by capillary absorption of synthetic urine having a surface tension of 65±5 dynes/cm.

The polymeric foams of the present invention can be prepared in the form of collapsed (i.e. un-expanded), polymeric foams that, upon contact with aqueous fluids, expand and absorb such fluids. These collapsed polymeric foams are usually obtained by expressing the water phase from the polymerized HIPE foam through compressive forces, and/or thermal drying and/or vacuum dewatering. After compression, and/or thermal drying/vacuum dewatering, the polymeric foam is in a collapsed, or un-expanded state.

Following compression and/or thermal drying/vacuum dewatering, the collapsed polymeric foam can re-expand when wetted with aqueous fluids. Surprisingly, these polymeric foams remain in this collapsed, or un-expanded state, for significant periods of time, e.g., up to at least about 1 year. The ability of these polymeric foams to remain in this collapsed/un-expanded state is believed to be due to the capillary forces, and in particular the capillary pressures developed within the foam structure. As used herein, "capillary pressures" refers to the pressure differential across the liquid/air interface due to the curvature of meniscus within the narrow confines of the pores in the foam. [See Chatterjee, "Absorbency," *Textile Science and Technology*, Vol. 7, 1985, p. 36.]

After compression, and/or thermal drying/vacuum dewatering to a practicable extent, these polymeric foams have residual water that includes both the water of hydration associated with the hydroscopic, hydrated salt incorporated therein, as well as free water absorbed within the foam. This residual water (assisted by the hydrated salts) is believed to exert capillary pressures on the resulting collapsed foam structure. Collapsed polymeric foams of the present invention can have residual water contents of at least about 4%, typically from about 4 to about 40%, by weight of the foam when stored at ambient conditions of 72° F. (22° C.) and 50% relative humidity. Preferred collapsed polymeric foams have residual water contents of from about 5 to about 25% by weight of the foam.

A key parameter of these foams is their glass transition temperature (Tg). The Tg represents the midpoint of the transition between the glassy and rubbery states of the polymer. Foams that have a higher Tg than the temperature of use can be very strong but will also be very rigid and potentially prone to fracture. Such foams also typically take a long time to recover to the expanded state when wetted with aqueous fluids colder than the Tg of the polymer after having been stored in the collapsed state for prolonged periods. The desired combination of mechanical properties, specifically strength and resilience, typically necessitates a fairly selective range of monomer types and levels to achieve these desired properties.

For foams of the present invention, the Tg should be as low as possible, so long as the foam has acceptable strength at in-use temperatures. Accordingly, monomers are selected as much as possible that provide corresponding homopolymers having lower Tg's. It has been found that the chain length of the alkyl group on the acrylate and methacrylate comonomers can be longer than would be predicted from the Tg of the homologous homopolymer series. Specifically, it has been found that the homologous series of alkyl acrylate or methacrylate homopolymers have a minimum Tg at a chain length of 8 carbon atoms. By contrast, the minimum Tg of the copolymers of the present invention occurs at a chain length of about 12 carbon atoms. (While the alkyl substituted styrene monomers can be used in place of the alkyl acrylates and methacrylates, their availability is currently extremely limited).

The shape of the glass transition region of the polymer can also be important, i.e., whether it is narrow or broad as a function of temperature. This glass transition region shape is particularly relevant where the in-use temperature (usually ambient or body temperature) of the polymer is at or near the Tg. For example, a broader transition region can mean an incomplete transition at in-use temperatures. Typically, if the transition is incomplete at the in-use temperature, the polymer will evidence greater rigidity and will be less resilient. Conversely, if the transition is completed at the in-use temperature, then the polymer will exhibit faster recovery from compression when wetted with aqueous fluids. Accordingly, it is desirable to control the Tg and the breadth of the transition region of the polymer to achieve the desired mechanical properties. Generally, it is preferred that the Tg of the polymer be at least about 10° C. lower than the in-use temperature. (The Tg and the width of the transition region are derived from the loss tangent vs. temperature curve from a dynamic mechanical analysis (DMA) measurement, as described in the Test Methods section hereafter).

B. Capillary Pressures and Forces Within Foam Structure

In its collapsed state, the capillary pressures developed within the foam structure at least equal the forces exerted by the elastic recovery or modulus of the compressed polymer. In other words, the capillary pressure necessary to keep the collapsed foam relatively thin is determined by the countervailing force exerted by the compressed polymeric foam as it tries to "spring back." The elastic recovery tendency of polymeric foams can be estimated from stress-strain experiments where the expanded foam is compressed to about 1/6 (17%) of its original, expanded thickness and then held in this compressed state until a relaxed stress value is measured. Alternatively, and for the purposes of the present invention, the relaxed stress value is estimated from measurements on the polymeric foam in its collapsed state when in contact with aqueous fluids, e.g., water. This alternative relaxed stress value is hereafter referred to as the "expansion pressure" of the foam. The expansion pressure for collapsed polymeric foams of the present invention is about 30 kilopascals (kPa) or less and typically from about 7 to about 20 kPa. A detailed description of a procedure for estimating the expansion pressure of foams is set forth in the TEST METHODS section of U.S. Pat. No. 5,387,207 (Dyer et al), issued Feb. 7, 1995, which is incorporated by reference.

For the purposes of the present invention, it has been found that the specific surface area per foam volume is particularly useful for empirically defining foam structures that will remain in a collapsed state. See U.S. Pat. No. 5,387,207 (Dyer et al), issued Feb. 7, 1995 (herein incorporated by reference), where specific area per foam volume is discussed in detail. "Specific surface area per foam volume" refers to the capillary suction specific surface area of the foam structure times its foam density in the expanded state. This specific surface area per foam volume value is characterized as "empirical" in that it is derived from (a) the capillary suction specific surface area that is measured during wetting of the dried foam structure, and (b) the density of the expanded foam structure after wetting to saturation, rather than by direct measurement of the dried, collapsed foam structure. Even so, it has been found that certain minimum specific surface area per foam volume values are correlatable to the ability of the foam structure to remain in a collapsed state. Polymeric foams according to the present invention having specific surface area per foam volume values of at least about 0.025 $m^2/cc$, preferably at least about 0.05 $m^2/cc$, most preferably at least about 0.07 $m^2/cc$, have been found empirically to remain in a collapsed state.

"Capillary suction specific surface area" is, in general, a measure of the test-liquid-accessible surface area of the polymeric network forming a particular foam per unit mass of the bulk foam material (polymer structural material plus solid residual material). Capillary suction specific surface area is determined both by the dimensions of the cellular units in the foam and by the density of the polymer, and is thus a way of quantifying the total amount of solid surface provided by the foam network to the extent that such a surface participates in absorbency.

The capillary suction specific surface area is particularly relevant to whether adequate capillary pressures are developed within the foam structure to keep it in a collapsed state until wetted with aqueous fluids. The capillary pressure developed within the foam structure is proportional to the capillary suction specific surface area. Assuming other factors such as the foam density and adhesion tension are constant, this means that, as the capillary suction specific surface area is increased (or decreased), the capillary pressure within the foam structure also increases (or decreases) proportionately.

For purposes of the present invention, capillary suction specific surface area is determined by measuring the amount of capillary uptake of a low surface tension liquid (e.g., ethanol) which occurs within a foam sample of a known mass and dimensions. A detailed description of such a procedure for determining foam specific surface area via the capillary suction method is set forth in the TEST METHODS section of U.S. Pat. No. 5,387,207 (Dyer et al), issued Feb. 7, 1995, which is incorporated herein by reference. Any reasonable alternative method for determining capillary suction specific surface area can also be utilized.

The collapsed polymeric foams of the present invention useful as absorbents are those that have a capillary suction specific surface area of at least about 3 $m^2/g$. Typically, the capillary suction specific surface area is in the range from about 3 to about 15 $m^2/g$, preferably from about 4 to about 13 $m^2/g$, most preferably from about 5 to about 11 $m^2/g$. Foams having such capillary suction specific surface area values (with expanded state densities of from about 0.010 to about 0.018 g/cc) will generally possess an especially desirable balance of absorbent capacity, fluid-retaining and fluid-wicking or distribution characteristics for aqueous fluids such as urine. In addition, foams having such capillary suction specific surface areas can develop a sufficient capillary pressure to keep the foam in a collapsed, un-expanded state until wetted or heated with such aqueous fluids or a specific type of heating means, e.g., a localized heating source such as a laser.

C. Free Absorbent Capacity

Another important property of the absorbent foams of the present invention is their free absorbent capacity. "Free absorbent capacity" is the total amount of test fluid (synthetic urine) which a given foam sample will absorb into its cellular structure per unit mass of solid material in the sample. To be especially useful in absorbent articles for absorbing aqueous fluids, the absorbent foams of the present invention should have a free absorbent capacity of from about 55 to about 100 mL, preferably from about 55 to about 75 mL of synthetic urine per gram of dry foam material. The procedure for determining the free absorbent capacity of the foam is described hereafter in the TEST METHODS section.

D. Expansion Factor

Upon exposure to aqueous fluids, the collapsed foams of the present invention expand and absorb the fluids. Upon exposure to a localized heat source, the collapsed, i.e., functional absorbent materials herein, expand. The foams of the present invention contain, in their expanded state, more fluid than most other foams. When these foams are compressively dewatered to a thickness of about ⅙ (17%) or less of their fully expanded thickness, they remain in even thinner states than is possible with prior HIPE foams, with a concomitant increase in storage efficiency and flexibility. This is attributable to the lower density of the expanded foams. The "expansion factor" for these foams is at least about 6×, i.e. the thickness of the foam in its expanded state is at least about 6 times the thickness of the foam in its collapsed state. The collapsed foams of the present invention typically have an expansion factor in the range of from about 6× to about 10×. By comparison, prior higher density foams typically have an expansion factor of only 4× to 5×.

For the purposes of the present invention, the relationship between expanded and collapsed thickness for compressively dewatered foams can be empirically predicted from the following equation:

$$\text{thickness}_{expanded} = \text{thickness}_{collapsed} \times 0.133 \times W{:}O \text{ ratio}$$

where $\text{thickness}_{expanded}$ is the thickness of the foam in its expanded state; $\text{thickness}_{collapsed}$ is the thickness of the foam in its collapsed state; and W:O ratio is the water-to-oil ratio of the HIPE from which the foam is made. Thus, a typical foam made from an emulsion with water-to-oil ratio of 60:1 would have a predicted expansion factor of 8.0, i.e., an expanded thickness 8 times the collapsed thickness of the foam. The procedure for measuring the expansion factor is described hereafter in the TEST METHODS section.

E. Resistance to Compression Deflection

An important mechanical feature of the absorbent polymeric foams of the present invention is their strength in their expanded state, as determined by its resistance to compression deflection (RTCD). The RTCD exhibited by the foams herein is a function of the polymer modulus, as well as the density and structure of the foam network. The polymer modulus is, in turn, determined by: a) the polymer composition; b) the conditions under which the foam is polymerized (for example, the completeness of polymerization obtained, specifically with respect to crosslinking); and c) the extent to which the polymer is plasticized by residual material, e.g., emulsifiers left in the foam structure after processing.

To be useful as absorbents in absorbent articles such as diapers, the foams of the present invention must be suitably resistant to deformation or compression by forces encountered in use when such absorbent materials are engaged in the absorption and retention of fluids. Foams which do not possess sufficient foam strength in terms of RTCD may be able to acquire and store acceptable amounts of body fluid under no-load conditions but will too easily give up such fluid under the compressive stress caused by the motion and activity of the user of the absorbent articles that contain the foam.

The RTCD exhibited by the polymeric foams of the present invention can be quantified by determining the amount of strain produced in a sample of saturated foam held under a certain confining pressure for a specified temperature and period of time. The method for carrying out this particular type of test is described hereafter in the TEST METHODS section. Foams useful as absorbents are those which exhibit an RTCD such that a confining pressure of 5.1 kPa produces a strain of typically about 40% or less compression of the foam structure when it has been saturated to its free absorbent capacity with synthetic urine having a surface tension of 65±5 dynes/cm. Preferably the strain produced under such conditions will be in the range from about 2 to about 25%, more preferably from about 4 to about 15%, most preferably from about 6 to about 10%.

F. Other Properties of Polymeric Foam

Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., average cell diameter, will often be specified.

A number of techniques are available for determining the average cell size of foams. The most useful technique, however, for determining cell size in foams involves a simple measurement based on the scanning electron photomicrograph of a foam sample. FIG. 1, for example, shows a typical HIPE foam structure according to the present invention in its expanded state. Superimposed on the photomicrograph is a scale representing a dimension of 20 $\mu$m. Such a scale can be used to determine average cell size via an image analysis procedure.

The cell size measurements given herein are based on the number average cell size of the foam in its expanded state, e.g., as shown in FIG. 1. The foams useful as absorbents for aqueous fluids in accordance with the present invention will preferably have a number average cell size of about 50 $\mu$m or less, and typically from about 5 to about 35 $\mu$m.

"Foam density" (i.e., in grams of foam per cubic centimeter of foam volume in air) is specified herein on a dry basis. The amount of absorbed water-soluble residual materials, e.g., residual salts and liquid left in the foam, for example, after HIPE polymerization, washing and/or hydrophilization, is disregarded in calculating and expressing foam density. Foam density does include, however, other water-insoluble residual materials such as emulsifiers present in the polymerized foam. Such residual materials can, in fact, contribute significant mass to the foam material.

Any suitable gravimetric procedure that will provide a determination of mass of solid foam material per unit volume of foam structure can be used to measure foam density. For example, an ASTM gravimetric procedure described more fully in the TEST METHODS section of U.S. Pat. No. 5,387,207 (Dyer et al), issued Feb. 7, 1995 (herein incorporated by reference) is one method that can be employed for density determination. In its collapsed state, polymeric foams of the present invention useful as absorbents have dry basis density values in the range of from about 0.1 to about 0.2 g/cc, preferably from about 0.11 to about 0.15 g/cc, and most preferably from about 0.12 to about 0.14 g/cc. In its expanded state, polymeric foams of the present invention useful as absorbents have dry basis density values in the range of from about 0.010 to about 0.018 g/cc, preferably from about 0.013 to about 0.018 g/cc.

Suitable absorbent foams will in general exhibit especially desirable and useful aqueous fluid handling and absorbency characteristics. The fluid handling and absorbency characteristics that are most relevant for absorbent foams are: A) the rate of vertical wicking of fluid through the foam structure; B) the absorbent capacity of the foam at specific reference wicking heights; and C) the ability of the absorbent foam structures to drain (partition) fluid from competing absorbent structures with which the foam can be in contact.

Vertical wicking, i.e., fluid wicking in a direction opposite from gravitational force, is an especially desirable performance attribute for absorbent foams herein. These foams will frequently be utilized in absorbent articles in a manner such that fluid to be absorbed must be moved within the article from a relatively lower position to a relatively higher position within the absorbent core of the article. Accordingly, the ability of these foams to wick fluid against gravitational forces is particularly relevant to their functioning as absorbent components in absorbent articles.

Vertical wicking is determined by measuring the time taken for a colored test liquid (e.g., synthetic urine) in a reservoir to wick a vertical distance of 5 cm through a test strip of foam of specified size. The vertical wicking procedure is described in greater detail in the TEST METHODS section of U.S. Pat. No. 5,387,207 (Dyer et al), issued Feb. 7, 1995, (herein incorporated by reference), but is performed at 31° C., instead of 37° C. To be especially useful in absorbent articles for absorbing urine, the foam absorbents of the present invention will preferably wick synthetic urine (65±5 dynes/cm) to a height of 5 cm in no more than about 30 minutes. More preferably, the preferred foam absorbents of the present invention wick synthetic urine to a height of 5 cm in no more than about 5 minutes.

The vertical wicking absorbent capacity test measures the amount of test fluid per gram of absorbent foam that is held within each one inch (2.54 cm) vertical section of the same standard size foam sample used in the vertical wicking test. Such a determination is generally made after the sample has been allowed to vertically wick test fluid to equilibrium (e.g., after about 18 hours). Like the vertical wicking test, the vertical wicking absorbent capacity test is described in greater detail in the TEST METHODS section of U.S. Pat. No. 5,387,207 (Dyer et al), issued Feb. 7, 1995, which is incorporated by reference.

Another important property of useful absorbent foams according to the present invention is their capillary absorption pressure. Capillary absorption pressure refers to the ability of the foam to wick fluid vertically. [See P. K. Chatterjee and H. V. Nguyen in "Absorbency," Textile Science and Technology, Vol. 7; P. K. Chatterjee, Ed.; Elsevier: Amsterdam, 1985; Chapter 2.] For the purposes of the present invention, the capillary absorption pressure of interest is the hydrostatic head at which the vertically wicked fluid loading is 50% of the free absorbent capacity under equilibrium conditions at 31° C. The hydrostatic head is represented by a column of fluid (e.g., synthetic urine) of height h. To be especially useful in absorbent articles for absorbing aqueous fluids, the preferred absorbent foams of the present invention will generally have a capillary absorption pressure of at least about 24.1 cm (9.5 inches). (Foams of the present invention typically have absorption pressures of from about 30 to about 40 cm.)

B. Absorbent Articles

By the term "absorbent article" it is meant herein a consumer product that is capable of absorbing urine or other fluids (i.e., liquids), like aqueous fecal matter (runny bowel movements), discharged by an incontinent wearer or user of the article. Examples of such absorbent articles include disposable diapers, incontinence garments, catamenials such as tampons and sanitary napkins, disposable training pants, bed pads, and the like. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad. A preferred embodiment of a unitary disposable absorbent article of the present invention is the catamenial pad, sanitary napkin 120, shown in FIG. 4. As used herein, the term "sanitary napkin" or "napkin" refers to devices which absorb and contain body exudates, and more specifically, refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other absorbent articles such as incontinence briefs, training pants, other feminine hygiene garments, disposable diapers and the like.

Figure 4:
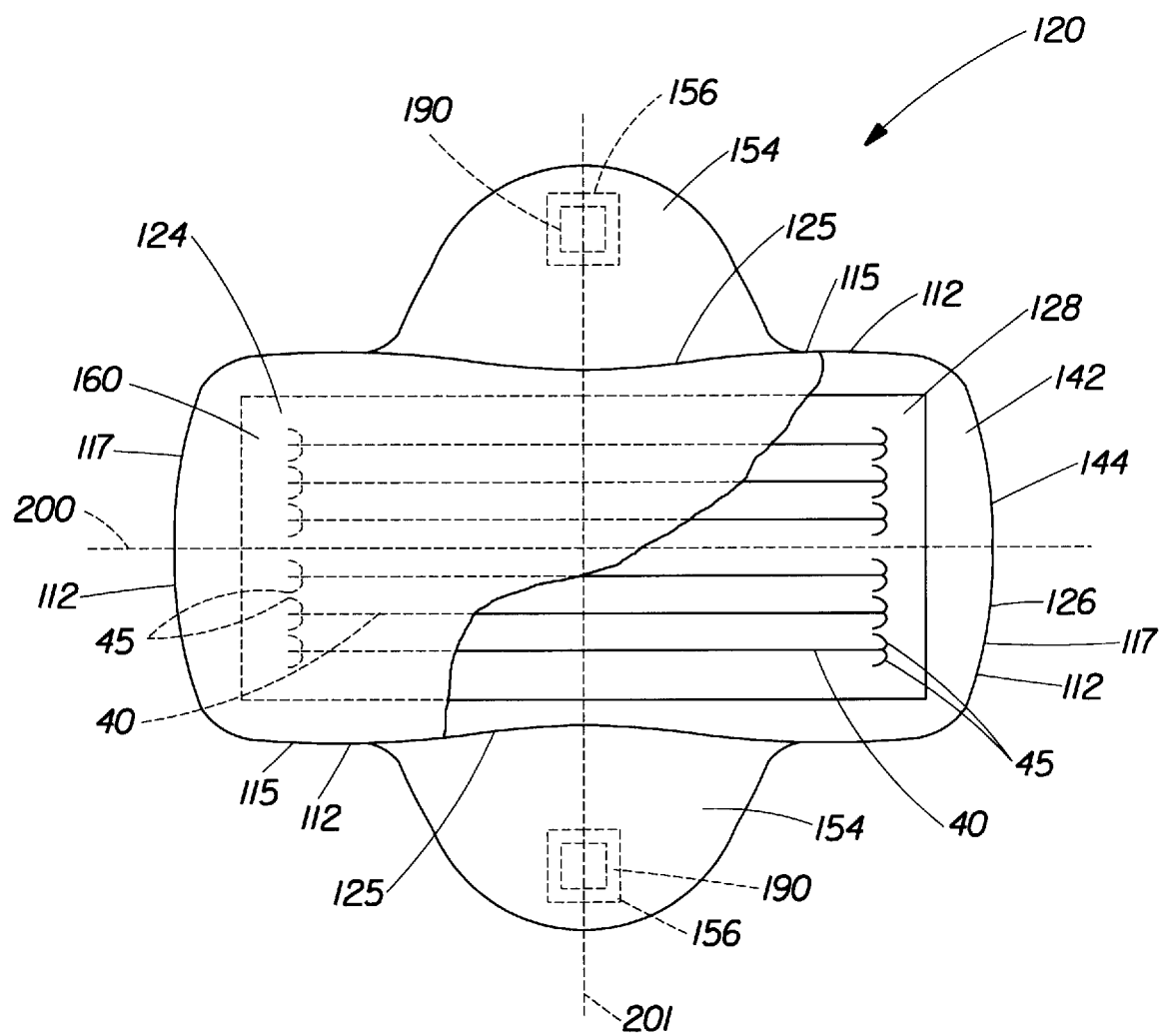
FIG. 4 shows a plan view of a preferred absorbent article herein.

FIG. 4 is a plan view of the sanitary napkin 120 of the present invention in its flat-out state with portions of the structure being cut-away to more clearly show the construction of the sanitary napkin 120 and with the portion of the sanitary napkin 120 which faces or contacts the wearer, oriented towards the viewer. As shown in FIG. 4, the sanitary napkin 120 preferably comprises a liquid pervious topsheet 124, a liquid impervious backsheet 126 joined with the topsheet 124, and an absorbent core 128 positioned between the topsheet 124 and the backsheet 126.

The sanitary napkin 120 has two surfaces, a body-contacting surface 160 or "body surface" and a garment surface 65 (not shown) facing oppositely to the topsheet 124. The sanitary napkin 120 is shown in FIG. 4 as viewed from its body surface. The body surface 160 is intended to be worn adjacent to the body of the wearer while the garment surface 165 (not shown) is on the opposite side and is intended to be placed adjacent to the wearer's undergarments when the sanitary napkin 120 is worn. The sanitary napkin 20 has two centerlines, a longitudinal centerline 200 and a transverse centerline 201. The term "longitudinal", as used herein, refers to a line, axis or direction in the plane of the sanitary napkin 120 that is generally aligned with (e.g., approximately parallel to) a vertical plane which bisects a standing wearer into left and right body halves when the sanitary napkin 120 is worn. The terms "transverse" or "lateral" as used herein, are interchangeable, and refer to a line, axis or direction which lies within the plane of the sanitary napkin 120 that is generally perpendicular to the longitudinal direction. FIG. 4 also shows that the sanitary napkin 120 has a periphery 112 which is defined by the outer edges of the sanitary napkin 120 in which the longitudinal edges are designated 115 and the end edges are designated 117.

While the topsheet, the backsheet, and the absorbent core may be assembled in a variety of well known configurations (including so called "tube" products or side flap products), preferred sanitary napkin configurations are described generally in U.S. Pat. No. 4,950,264, "Thin, Flexible Sanitary Napkin" issued to Osborn on Aug. 21, 1990; U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987. Each of these patents are hereby incorporated herein by reference. FIG. 4 shows a preferred embodiment of the sanitary napkin 120 in which the topsheet 124 and the backsheet 126 have length and width dimensions generally larger than those of the absorbent core 128. The topsheet 124 and the backsheet 126 extend beyond the edges of the absorbent core 128 to thereby form not only portions of the periphery but also side flaps 154.

The backsheet 126 and the topsheet 124 are positioned adjacent the garment surface and the body surface, respectively, of the absorbent core 128 and are preferably joined thereto and to each other by attachment means (not shown) such as those well known in the art. For example, the backsheet 126 and/or the topsheet 124 may be secured to the absorbent core 128 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 126 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 126 has an inner surface 142 and an outer surface 144 opposed to the inner surface 142. The backsheet 126 prevents the exudates absorbed and contained in the absorbent core 128 from wetting articles which contact the sanitary napkin 120 such as pants, pajamas and undergarments. The backsheet 126 may thus comprise a woven or nonwoven material, polymeric films such as thermoplastic films of polyethylene or polypropylene, or composite materials such as a film-coated nonwoven material. Preferably, the backsheet 126 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar, Incorporated, of Terre Haute, Ind., under the designation XP-39385. The backsheet 126 is preferably embossed and/or matte finished to provide a more clothlike appearance. Further, the backsheet 126 may permit vapors to escape from the absorbent core 128 (i.e., breathable) while still preventing exudates from passing through the backsheet 126.

The topsheet 124 is compliant, soft feeling, and non-irritating to the wearer's skin. Further, the topsheet 124 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., pending, which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

In use, the sanitary napkin 120 is held in place in a wearer's undergarment by an attachment system 189 (not shown) secured to the outer surface 144 of the backsheet 126. The attachment system 189 may comprise any support means or attachment means well-known for such purposes. A suitable attachment system 189 is adhesive layer 190, sometimes called panty fastening adhesive. The adhesive layer 190 provides a means for securing the sanitary napkin 120 in the crotch portion of the panty. Thus, a portion of or all of the outer surface 144 of the backsheet 126 is coated with adhesive layer 190. Any adhesive or glue used in the art for such purposes can be used for the adhesive 190 herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the sanitary napkin 120 is placed in use, the pressure-sensitive adhesive layer 190 is typically covered with a removable release liner 156 in order to keep the adhesive layer from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. In a preferred embodiment, the sanitary napkin 120 of the present invention is used by removing the release liner 156, and thereafter placing the sanitary napkin 120 in a panty so that the adhesive layer 190 contacts the panty. As one function, the adhesive layer 190 maintains the sanitary napkin 120 in its position within the panty during use.

In a preferred embodiment of the present invention, FIG. 4 shows the sanitary napkin having two flaps 154 each of which are adjacent to and extend laterally from the side edges of the absorbent core 128. The flaps 154 are configured to drape over the edges of the wearer's panties in the crotch region so that the flaps 154 are disposed between the edges of the wearer's panties and the thighs. The flaps 154 serve at least two purposes. First, the flaps help serve to prevent soiling of the wearer's body and panties by menstrual fluid, preferably by forming a double wall barrier along the edges of the panty. Second, the flaps 154 are preferably provided with attachment means on their garment surface so that the flaps 154 can fold back under the panty and attach to the garment facing side of the panty or one flap 154 to another. In this way, the flaps 154 serve to keep the sanitary napkin 120 properly positioned in the panty.

The flaps 154 can be constructed of various materials including materials similar to the topsheet 124, backsheet 126, tissue, or combination of these materials. Further, the flaps 154 may be a separate element attached to the main body of the napkin 120 or can comprise extensions of the topsheet 124 and backsheet 126 (i.e., a unitary construction). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. Each of these patents are incorporated herein by reference.

Polymeric foams of the present invention are particularly useful as at least a portion of the absorbent structures (e.g., absorbent cores) for various absorbent articles. The absorbent foam structures herein are particularly suitable for use in articles such as catamenial pads, diapers, incontinence pads or garments, clothing shields, and the like.

In its simplest form, an absorbent article of the present invention need only include a backing sheet, preferably liquid-impervious, and one or more absorbent foam structures associated with this backing sheet. The absorbent foam structure and the backing sheet will be associated in such a manner that the absorbent foam structure is situated between the backing sheet and the fluid discharge region of the wearer of the absorbent article. Liquid impervious backing sheets can comprise any material; for example polyethylene or polypropylene, having a thickness of about 1.5 mils (0.038 mm), which will help retain fluid within the absorbent article.

The absorbent core 128 of the absorbent article embodiments of the present invention can consist solely of one or more of these foam structures. For example, the absorbent core can comprise a single unitary piece of foam shaped as desired or needed to best fit the type of absorbent article in which it is to be used. Alternatively, the absorbent core can comprise a plurality of foam pieces or particles that can be adhesively bonded together or which can simply be constrained into an unbonded aggregate held together by an overwrapping of envelope tissue or by means of the topsheet and backing sheet of the absorbent article.

The absorbent core 128 of the absorbent articles herein can also comprise other, e.g., conventional, elements or materials in addition to one or more absorbent foam structures of the present invention. For example, absorbent articles herein can utilize an absorbent core that comprises a combination, e.g., an air-laid mixture, of particles or pieces of the absorbent foam structures herein and conventional absorbent materials such as a) wood pulp or other cellulosic fibers, and/or, b) particles or fibers of polymeric gelling agents.

In one embodiment involving a combination of the absorbent foam herein and other absorbent materials, the absorbent articles can employ a multi-layer absorbent core configuration where a core layer containing one or more foam structures of the present invention can be used in combination with one or more additional separate core layers comprising other absorbent structures or materials. These other absorbent structures or materials, for example, can include air-laid or wet-laid webs of wood pulp or other cellulosic fibers. These other absorbent structures can also comprise other types of foams, e.g., absorbent foams or even sponges useful as fluid acquisition/distribution components such as those disclosed in U.S. Pat. No. 5,563,179 issued to DesMarais, et al., which is hereby incorporated by reference. These other absorbent structures can also contain, for example up to 80% by weight, of particles or fibers of polymeric gelling agent of the type commonly used in absorbent articles that are to acquire and retain aqueous fluids. Polymeric gelling agents of this type and their use in absorbent articles are more fully described in U.S. Reissue Pat. No. 32,649 (Brandt et al), reissued Apr. 19, 1988, which is incorporated by reference.

An embodiment of these absorbent articles utilizes a multi-layer absorbent core having a fluid handling layer positioned in the fluid discharge region of the wearer of the article. This fluid-handling layer can be in the form of a high loft nonwoven, but is preferably in the form of a fluid acquisition/distribution layer comprising a layer of modified cellulosic fibers, e.g., stiffened curled cellulosic fibers, and optionally up to about 10% by weight of this fluid acquisition/distribution layer of polymeric gelling agent. The modified cellulosic fibers used in the fluid acquisition/distribution layer of such a preferred absorbent article are preferably wood pulp fibers that have been stiffened and curled by means of chemical and/or thermal treatment. Such modified cellulosic fibers are of the same type as are employed in the absorbent articles described in U.S. Pat. No. 4,935,622 (Lash, et al.), issued Jun. 19, 1990, which is incorporated herein by reference.

These multi-layer absorbent cores also comprise a second, i.e., lower, fluid storage/redistribution layer comprising a foam structure of the present invention. For purposes of the present invention, an "upper" layer of a multi-layer absorbent core is a layer that is relatively closer to the body of the wearer, e.g., the layer closest to the article topsheet. The term "lower" layer conversely means a layer of a multi-layer absorbent core that is relatively further away from the body of the wearer, e.g., the layer closest to the article backsheet. This lower fluid storage/redistribution layer is typically positioned within the absorbent core so as to underlie the (upper) fluid-handling layer and be in fluid communication therewith. Absorbent articles that can utilize the absorbent foam structures of the present invention in a lower fluid storage/redistribution layer underlying an upper fluid acquisition/distribution layer containing stiffened curled cellulosic fibers are described in greater detail in U.S. Pat. No. 5,147,345 (Young, et al.), issued Sep. 15, 1992 which is incorporated herein by reference. Multi-layer absorbent cores can also be made according to commonly assigned U.S. application Ser. No. 08/521,556, pending, entitled Absorbent Articles For Fluid Management (Gary Dean Lavon, et al.), filed Aug. 30, 1995 (herein incorporated by reference), where the fluid storage/redistribution layer comprises an absorbent foam according to the present invention.

Disposable napkins comprising the absorbent foam structures of the present invention can be made by using conventional techniques, but by replacing or supplementing the wood pulp fiber web ("airfelt") or modified cellulosic core absorbents typically used in conventional diapers with one or more foam structures of the present invention. Foam structures of the present invention can thus be used in diapers in single layers, or in various multiple layered core configurations as previously described.

Another embodiment herein provides a method of altering (or profiling) a functional absorbent material from at least its top surface within an assembled absorbent article. The method comprises the steps of delivering an absorbent article comprising a topsheet, a backsheet joined to the topsheet, and a functional absorbent material that is positioned between the topsheet and the backsheet to a localized heating source. Heat is applied to the localized heating source through the topsheet to the functional absorbent material such that the localized heating source provides localized heating to the functional absorbent material to finitely expand a material in regions immediately surrounding points of application of the localized heating.

In the above method, the laser used to score or expand the functional absorbent material is set at specified power and intensity levels and laser beam diameters that will allow the laser to pass through the topsheet or backsheet to the functional absorbent material. That is, the laser will pass through the topsheet or backsheet without scoring, cutting, aperturing or burning the topsheet or backsheet material. Preferably, the topsheet or backsheet will experience only minimal heat transfer from the laser and most preferably no heat will be transferred at all.

Another type of absorbent article which can utilize the absorbent foam structures of the present invention comprises form-fitting products such as training pants. Such form-fitting articles will generally include a nonwoven, flexible substrate fashioned into a chassis in the form of briefs or shorts. An absorbent foam structure according to the present invention can then be affixed in the crotch area of such a chassis in order to serve as an absorbent "core". This absorbent core will frequently be over-wrapped with envelope tissue or other liquid pervious, nonwoven material. Such core overwrapping thus serves as the "topsheet" for the form-fitting absorbent article.

The flexible substrate which forms the chassis of the form-fitting article can comprise cloth or paper or other kinds of nonwoven substrates or formed films and can be elasticized or otherwise stretchable. Leg bands or waist bands of such training pant articles can be elasticized in conventional fashion to improve fit of the article. Such a substrate will generally be rendered relatively liquid-impervious, or at least not readily liquid-pervious, by treating or coating one surface thereof or by laminating this flexible substrate with another relatively liquid-impervious substrate to thereby render the total chassis relatively liquid-impervious. In this instance, the chassis itself serves as the "backsheet" for the form-fitting article. Typical training pant products of this kind are described in U.S. Pat. No. 4,619,649 (Roberts), issued Oct. 28, 1986, which is incorporated herein by reference.

As previously discussed, lasers are the preferred heat source for the invention herein. All "lasers" (i.e., standing for light amplification by stimulated emission of radiation) are sources of light, and specifically are forms of electromagnetic radiation which propagates at a velocity of $3 \times 10^{10}$ cm/s and are characterized by oscillating electric fields.

While many laser types may be suitable for the heating described herein, gas lasers are preferable for such heating. Gas lasers have many advantages. First, the gas used therein to generate laser light emissions is homogenous. Also, the removal of heat, an important consideration in laser design, is relatively easy, because the heated gas can flow out of the region where laser action occurs.

A preferable gas laser used herein is a $CO_2$ laser. A $CO_2$ laser can either provide a continuous or pulsed laser emission. This laser type has had industrial uses in welding, drilling, heating and heat treating. The $CO_2$ laser is a molecular laser that operates on molecular energy levels and uses a mixture of carbon dioxide, nitrogen and helium. Operation of the carbon dioxide laser involves the excitation of vibrational levels of the nitrogen laser by collisions with electrons in the electrical discharge, followed by resonant energy transfer to a vibrational level of the carbon dioxide molecule.

The $CO_2$ laser is extremely useful for heating the functional absorbent material of the invention herein because a $CO_2$ laser beam is focused on a functional absorbent material herein, vaporizes at least the surface layer thereby causing the material to be cut or apertured. Within the functional absorbent material heat is transferred from the points of heat application. This heating causes the material in the immediately surrounding region of the functional absorbent material to expand. The amount of cut, and expansion, is related to web speed, laser power and laser focusing. As previously discussed in detail, discrete "barriers" or "channels" can be formed with this method.

In another application of the use of a laser, a $CO_2$ laser beam may be so focused on a functional absorbent material as to only cut or score the functional absorbent material to a certain prescribed depth. This cut-depth is related to web speed, laser power and laser focusing. By orienting the cuts in a particular pattern the acquisition properties of the material can be improved. Also, the cuts increase the available surface area of the material (increasing acquisition) and also impede the motion of fluid-like material (such as runny BM) which allow for more acquisition time.

Both of the above mentioned methods can use a stationary beam in either continuous or intermittent operation to make machine direction cuts in the functional absorbent material. Alternatively, the above methods can use a guided laser beam (continuous or intermittent) to provide any combination or number of patterns as are partially shown in FIGS. 3A to 3D. In yet another embodiment, multiple beams can be used to make more rapid modifications and varying configurations to these materials. Neither the size of the cuts nor the configurations of any laser cutting herein to form channels forms any part of the invention herein, and it is clear that one skilled in the art may modify such to his/her own desired specifications.

Material properties and laser wavelengths can be adjusted to enhance the absorption of the laser energy to encourage cutting, or adjusted to lessen the absorption of laser energy to make the material "transparent" to the laser energy. In a multi-layered structure, e.g., an absorbent article, it is feasible to have the laser pass through an upper layer of material without affecting it and then cut (or modify) a material below the first material. Modifications could be made within an already assembled product, e.g. an assembled sanitary napkin traveling down a production line.

An alternative type of gas laser that can be used herein is an excimer laser. Excimer lasers represent laser technology in the ultraviolet portion of the light spectrum offering the capability of pulsed short-wavelength lasers having high peak power. A leading example of excimer lasers is the krypton fluoride laser.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of altering a functional absorbent material from at least a top surface thereof, said method comprising the steps of:

providing a localized heating source to said functional absorbent material; and expanding said functional absorbent material in finite regions immediately surrounding said localized heating source by applying said localized heating source to said functional absorbent material.

2. The method of claim 1 wherein said localized heating source comprises a laser.

3. The method of claim 2 wherein said laser is a $CO_2$ laser.

4. The method of claim 1 wherein said localized heating source comprises at least one hot-edged knife.

5. The method of claim 1 wherein said functional absorbent material is heated about discrete lines of heating, said lines of heating being partially cut into said functional absorbent material to form flow channels for fluid transport.

6. The method of claim 5 wherein each said flow channel is bordered by at least two expanded regions of said functional absorbent material, said expanded regions providing partial containment of fluid flow about each said flow channel.

7. The method of claim 5 wherein each said expanded region is substantially juxtaposed and parallel to said lines of heating.

8. The method of claim 7 wherein said partially cut line of heating comprises a hinge means about which said functional absorbent material folds.

9. The method of claim 8 wherein said functional absorbent material comprises a plurality of said hinge means formed from a plurality of partially cut lines of heating.

10. The method of claim 1 wherein said functional absorbent material is heated at discrete points such that a region of functional absorbent material expands substantially circumferentially about each said discrete point of heating, thereby forming a circular barrier means for holding fluids and solids therein.

11. A method of altering a functional absorbent material from at least a top surface thereof within an absorbent article, said method comprising the steps of:

delivering an absorbent article comprising a topsheet, a backsheet joined to said topsheet, and a functional absorbent material being positioned between said topsheet and said backsheet to a localized heating source; and expanding said functional absorbent material in finite regions immediately surrounding said localized heating source by applying said localized heating source to said functional absorbent material.

12. The method of claim 11 wherein said localized heating source comprises a laser.

13. The method of claim 12 wherein said laser is a $CO_2$ laser.

14. The method of claim 11 wherein said functional absorbent material is heated about discrete lines of heating, said lines of heating being partially cut into said functional absorbent material to form flow channels for fluid transport.

15. The method of claim 14 wherein each said flow channel is bordered by at least two expanded regions of said functional absorbent material, said expanded regions providing partial containment of fluid flow about each said flow channel.

16. The method of claim 15 wherein each said expanded region is substantially juxtaposed and parallel to said lines of heating.

17. The method of claim 16 wherein said partially cut line of heating comprises a hinge means about which said functional absorbent material folds.

18. The method of claim 17 wherein said functional absorbent material comprises a plurality of said hinge means formed from a plurality of partially cut lines of heating.

19. The method of claim 11 wherein said functional absorbent material is heated at discrete points such that a region of functional absorbent material expands substantially circumferentially about each said discrete point of heating, thereby forming a circular barrier means for holding fluids and solids therein.

* * * * *